(12) United States Patent
Chaddock et al.

(10) Patent No.: US 7,193,066 B1
(45) Date of Patent: Mar. 20, 2007

(54) PREPARATION OF HIGHLY PURE TOXIN FRAGMENTS

(75) Inventors: John Andrew Chaddock, Salisbury (GB); Frances Celine Gail Alexander, Salisbury (GB); Keith Alan Foster, Salisbury (GB)

(73) Assignee: The Health Protection Agency (GB)

( * ) Notice: Subject to any disclaimer, the term of this patent is extended or adjusted under 35 U.S.C. 154(b) by 450 days.

(21) Appl. No.: 10/070,764

(22) PCT Filed: Sep. 13, 2000

(86) PCT No.: PCT/GB00/03519

§ 371 (c)(1),
(2), (4) Date: Mar. 12, 2002

(87) PCT Pub. No.: WO01/19863

PCT Pub. Date: Mar. 22, 2001

(30) Foreign Application Priority Data

Sep. 13, 1999 (GB) ................................ 9921592.3

(51) Int. Cl.
*C07K 1/00* (2006.01)
*G01N 33/537* (2006.01)
*G01N 33/549* (2006.01)

(52) U.S. Cl. ...................... 530/413; 530/416; 530/417; 530/810; 530/811; 436/538; 436/532

(58) Field of Classification Search ................ 530/413, 530/416, 417, 388.4, 810, 811, 387.9; 436/535, 436/538, 532
See application file for complete search history.

(56) References Cited

U.S. PATENT DOCUMENTS 5,601,826 A 2/1997 Halpern .................. 424/190.1

FOREIGN PATENT DOCUMENTS

| DE | 40 37 809 A1 | 6/1992 |
|----|--------------|--------|
| WO | WO 96/12802 | 5/1996 |
| ZA | 9803690 A | 2/1999 |

OTHER PUBLICATIONS

Rosetto et al. Biochem. J. 285: 9-12, 1992.*
Hallis et al. In: Botulinum and Tetanus Neurotoxins. (Ed) DasGupta et al. Plenum Press, New York, pp. 433-436, 1993.*
Gimenez, J.A. and DasGupta, B.R., "Botulinum Type A Neurotoxin Digested with Pepsin Yields 132, 97, 72, 45, 42, and 18 kD Fragments," *J. Pro. Chem. 12*:351-363, Plenum Publishing Corporation (1993).
Schiavo, G. et al., "Botulinum Neurotoxins Are Zinc Proteins," *J. Biol. Chem. 267*:23479-23483, The American Society for Biochemistry and Molecular Biology, Inc. (1992).
Derwent Patent Abstract. File No. 351, Accession No. 9065531, English language abstract of DE 4037809A.

* cited by examiner

*Primary Examiner*—S. Devi
(74) *Attorney, Agent, or Firm*—Sterne, Kessler, Goldstein & Fox P.L.L.C.

(57) ABSTRACT

Toxin derivatives are prepared by proteolytic treatment of holotoxin, and their toxicity is reduced by contacting the preparation with a ligand, which can be a metal or an antibody or another ligand. This ligand selectively binds to the toxin but not to the toxin derivative. Removing the ligand and toxin bound to the ligand further reduces toxicity. A second ligand is used to remove conjugates of the toxin and the first ligand. Compositions contain the purified derivative, optionally plus the toxin and the ligand.

10 Claims, 5 Drawing Sheets

FIG. 1

SDS-PAGE analysis of LH$_N$/A purified by immunoaffinity approach

FIG. 1(contd.)

FIG. 2
Cleavage of SNAP-25 by $LH_N/A$

FIG. 3

Inhibition of neurotransmitter release from eSCN by $LH_N/A$ and BoNT/A

% inhibition 3[H]-glycine release vs pM

FIG. 4
Mouse toxicity data for purified vs. standard $LH_N/A$

| | Mean number of survivors (/4) | | |
|---|---|---|---|
| | 50μg/mouse | 20μg/mouse | 5μg/mouse |
| Immunocolumn strategy (n=15) | 1.60±0.41 | 3.67±0.16 | ND |
| IMAC strategy (n=3) | 1.33±0.88 | 3.33±0.33 | ND |
| Mono Q® only (n=3) | 0 | 0 | 1.33±1.33 |

PREPARATION OF HIGHLY PURE TOXIN FRAGMENTS

CROSS REFERENCE TO RELATED APPLICATIONS

The present application is a national phase entry under 35 U.S.C. § 371 of International Patent Application No. PCT/GB00/03519 filed on Sep. 13, 2000, and published in English on Mar. 22, 2001. International Patent Application No. PCT/GB00/03519 claims priority to GB 9921592.3, filed Sep. 13, 1999.

BACKGROUND OF THE INVENTION

1. Field of the Invention

This invention relates to derivatives, such as fragments, of toxins, particularly clostridial neurotoxins. It also relates to preparations containing those derivatives and to methods of obtaining the derivatives and the preparations.

2. Description of the Related Art

The clostridial neurotoxins are proteins with molecular masses of the order of 150 kDa. They are produced by various species of bacterium of the genus *Clostridium*, most importantly *C. tetani* and several strains of *C. botulinum*. There are at present eight neurotoxins known: tetanus toxin, and botulinum neurotoxin in its serotypes A, B, $C_1$, D, E, F and G, and they all share similar structures and modes of action. The clostridial neurotoxins are synthesised by the bacterium as a single polypeptide that is modified post-translationally to form two polypeptide chains joined together by a disulphide bond. The two chains are termed the heavy chain (H), which has a molecular mass of approximately 100 kDa, and the light chain (L), which has a molecular mass of approximately 50 kDa.

The clostridial neurotoxins bind to an acceptor site (Black, J. D. & Dolly, J. O., Neuroscience, 23, 767–779, 1987 and Dolly et al. in Cellular and Molecular Basis of Cholinergic Function, ed. Dowdall, M. J. & Hawthorne, J. N., Chapter 60, 1987) on the cell membrane of the motoneurone at the neuromuscular junction and are internalised by an endocytotic mechanism (Montecucco et al., Trends Biochem. Sci., 11, 314, 1986). It is believed that the clostridial neurotoxins are highly selective for motoneurons due to the specific nature of the acceptor site on those neurones. The binding activity of clostridial neurotoxins is known to reside in a carboxy-terminal region of the heavy chain component of the dichain neurotoxin molecule, a region known as $H_C$. The N-terminal region of the H-chain ($H_N$ domain) is thought to be of central importance in the translocation of the L-chain into the cytosol and has been demonstrated to from channels in lipid vesicles (Shone et al, Eur. J. Biochem. 167, 175–180).

Clostridial neurotoxins possess a highly specific zinc-dependent endopeptidase activity that is known to reside in the L-chain. Each toxin serotype hydrolyses a specific peptide bond within one of three proteins of the SNARE complex; VAMP (synaptobrevin), syntaxin or SNAP-25. Proteolytic cleavage of one of these proteins leads to instability of the SNARE complex and consequent prevention of vesicular release. The enzymatic activity of the light chain of the neurotoxin leads to inhibition of neurotransmitter release, which results in a prolonged muscular paralysis.

The central role of the SNARE proteins in regulated secretion has been convincingly established (e.g. Niemann et al., (1994) *Trends Cell Biol.*, 4, 179–185). However, the correlation of SNARE protein involvement with the release of specific hormones, peptides, transmitters and other signalling molecules remains to be established in the majority of cases. The range of highly specific endopeptidase activities of clostridial neurotoxin serotypes provides a unique approach to the understanding of SNARE-mediated events. Unfortunately, the use of native clostridial toxins for the study of such events is limited by at least two important aspects. Firstly, the expression of the requisite toxin receptor is restricted to a limited population of cells, thereby limiting the range of cell types in which SNARE-mediated events can be studied without cellular disruption. Secondly, the significant hazards associated with working with potent neurotoxins lead to restrictions on the range of applications and experimental design. Clostridial neurotoxins are the most potent neuroparalytic toxins known and must be manipulated in specialised laboratory conditions by specially trained and, preferably, vaccinated staff. The ability to produce highly purified non-toxic fragments of clostridial neurotoxins possessing the enzymatic activity of the clostridial neurotoxins and capable of delivery to the cytosol of selected cells would therefore provide a valuable tool for studying secretory mechanisms.

The ability of the clostridial neurotoxins' enzymatic activity to destabilise SNARE complex formation and thereby inhibit vesicle fusion at the plasma membrane also has therapeutic potential. A number of therapeutic applications have been proposed (e.g. WO 96/33273 & WO 94/21300) that are dependent on the successful retargeting of clostridial neurotoxin fragments. These approaches require a source of non-hazardous neurotoxin fragment that is suitable for the synthesis of non-toxic conjugates, since the side effect profile of a therapeutic contaminated with neurotoxin would be unacceptably high. In addition to retargeting of clostridial toxin fragments, there are further applications for non-toxic clostridial derivatives. For example, as an immunogen for vaccine preparation, as a source of material from which highly purified neurotoxin-related fragments can be prepared, and as a non-toxic endopeptidase standard in diagnostic kits (e.g. WO 95/33850).

Since the cell binding function of clostridial neurotoxins resides in the $H_C$ domain of the heavy chain, generation of a fragment in which the binding capability of the $H_C$ has been deleted but the properties of the $H_N$ domain are retained ($LH_N$) is potentially a suitable method for the production of a non-toxic derivative.

It is known to prepare these fragments by proteolytic treatment of toxin and then separation of toxin from fragments by anion exchange chromatography, and such methods successfully yield fragments that are 99.99% pure.

A central or recurrent problem associated with obtaining or using products from toxins made by these methods is the risk of residual toxicity in those products. It would hence be desirable to provide a method of removing toxin from such products. However, existing protocols have reached the limits of their abilities in this respect.

For example, it has been observed that the known fragments often exhibit a high inhibition of neurotransmitter release by neuronal cells in vitro. This has hampered investigation into the properties of conjugates in which a toxin fragment is combined with a ligand providing a specific targeting function, because of difficulty in providing controls against which to judge the conjugate activity.

DETAILED DESCRIPTION OF THE INVENTION

It is an object of the present invention to provide a method of preparing a toxin derivative preparation. A further object of the invention is to provide a method of removing toxin from a toxin derivative preparation.

It has been discovered in accordance with the present invention that existing toxin derivative preparations, though considered to be pure, and though containing toxin at an extremely low level, nevertheless contain sufficient residual toxin to interfere with the applications of the fragment, conjugate or other toxin derivative.

Thus, in a first aspect of the invention, there is provided a method of reducing toxicity of a toxin derivative preparation, comprising contacting said preparation with a ligand which selectively binds to the toxin but not to the toxin derivative.

In a use of the invention, the ligand binds to and effectively neutralises residual toxin which is contaminating the toxin derivative preparation. The ligand preferentially binds to the toxin compared with its binding to the derivative. Thus in use there may be some small loss of derivative at the same time as toxin binds to the ligand. It has been found that prior art preparations of toxin derivatives may contain toxin at levels of one toxin molecule per 10,000 toxin fragments, and even at this low level the toxin adversely effects the uses of the fragment. According to the invention, an antibody that preferentially binds to the toxin, but not to the derivative, can be used to reduce or remove toxicity associated with the toxin, thereby enabling the effects and applications of the derivative to be examined and used without any masking effect of the residual toxin.

In an embodiment of the invention, described in more detail below, a toxin fragment prepared according to prior art methods significantly inhibited substance P release from dorsal root ganglia. This inhibition was reduced almost entirely by the combination of the fragment with an antibody that specifically bound to toxin.

Antibodies for use in the present invention can be prepared using polyclonal or monoclonal techniques. Suitable methodology is found for example in "Antibodies: A laboratory manual, by Ed Harlow and David Lane, 1988". Monoclonal antibodies can be prepared by immunising mice against toxin, harvesting lymphocyte cells from the spleens of immunised mice and fusing these with myeloma cells. Antibodies secreted by the resulting hybridomas are screened for binding to toxin and positive clones selected and propagated. Monoclonal antibodies are harvested from cultured hybridomas and purified using chromatographic methods—see for example Pharmacia handbook on "Monoclonal antibody purification". As an alternative to immunising mice with the toxin itself, the mice can be immunised with a different source of a $H_c$ domain, whether obtained from native material or expressed in an alternative, non clostridial, host. Alternatively, mice can be immunised with toxoided preparations of intact neurotoxins and the anti Hc antibodies selected. This may be achieved in at least 2 ways for example: specific Hc antisera may be bound to immobilised Hc and subsequently eluted for use. Conversely, specific Hc antisera may be obtained by adsorbing non-Hc antisera onto $LH_N$.

This invention thus provides, in specific examples, preparation of specific, defined fragments from native clostridial neurotoxins. Purified clostridial neurotoxin obtained from Clostridia sp. using previously reported techniques (for example, Shone, C. C. and Tranter, H. S. (1995) in "Clostridial Neurotoxins—The molecular pathogenesis of tetanus and botulism", (Montecucco, C., Ed.), pp. 152–160, Springer) can be fragmented by proteolytic or chemical cleavage to yield a crude mixture of derivatives that possess elements of the light chain, heavy chain or both (Gimenez, J. A. & DasGupta, B. R. (1993) J. Protein Chem., 12, 351–363; Shone, C. C., Hambleton, P. and Melling, J. (1987) Eur. J. Biochem. 167, 175–180). Classical chromatographic techniques are used to separate the crude mixture into partially purified fragments, the residual toxicity of which would make them unsuitable for many applications, and the fragments are then combined with a neutralizing ligand.

During testing by the inventors of a conjugate or a toxin fragment with a targeting ligand, it was not possible in vitro to determine the selectivity of an $LH_N$ fragment, though the reasons for this were not known to the inventors at the time. According to the invention, it has surprisingly been found that very low levels of toxins present were masking the $LH_N$ fragment activity, and now advantageously it is possible further to reduce this toxin content so that pure $LH_N$ activity can be measured and assessed.

In the particular case of in vivo uses of fragments and conjugates and other derivatives, a specific embodiment of the invention, described in more detail below, determined that fragments according to the present invention exhibited a level of toxicity that was more than 10 times lower than that of the prior art fragments, which prior art fragments were hitherto considered as being pure and toxin-free.

It is a preferred additional step in the method of the invention to separate the ligand from the toxin derivative preparation.

In one embodiment of the invention, a specific binding event between an immobilised matrix and a domain present on the neurotoxin, but absent from the fragment, is used to separate neurotoxin from the fragment. Such a method is used specifically to bind neurotoxin and other fragments possessing the requisite binding domain from a crude neurotoxin fragment mixture. Non-binding fragments that are free of neurotoxin are simply isolated from the column flow through. Binding fragments including neurotoxin can be isolated by altering the conditions of binding, for instance by altering the chemical environment (e.g. pH, ionic strength) or incorporation of a substance that competes for the binding site (e.g. peptide, sugar moiety). One suitable example is a column containing the natural receptor, or a version of the receptor, for which the neurotoxin has an affinity. This receptor may be purified and immobilised to a matrix for use in a column or free in solution, or present in a preparation of cells or cell membrane, and is of use for purification of $LH_N$. Typically, a crude preparation of clostridial neurotoxin fragments is applied to the receptor preparation to bind neurotoxin and other fragments that possess receptor binding properties. Non-binding fragments, which include $LH_N$, are recovered from the receptor preparation by simple elution. Binding fragments and neurotoxin are released and harvested as described above.

Purification of clostridial endopeptidases is also suitably achieved according to the invention using metal ion chromatography. Clostridial endopeptidases are characterised as metalloendopeptidases due to the co-ordination of a metal ion at the active site of the enzyme. Given this specific metal ion binding capacity of clostridial neurotoxins, it might be predicted that both neurotoxin and endopeptidase fragments bind to immobilised metal resin via this catalytic site interaction. However, it is found that the $LH_N$ does not bind to the chelating column whereas the neurotoxin does. In an example, set out in more detail below, a method for the purification of $LH_N/A$ utilises immobilised zinc ions to bind BoNT/A and purify $LH_N/A$. The low toxicity of $LH_N/A$ purified by this method is also confirmed below.

Another embodiment of the invention comprises immobilising specific antibodies to a column resin. The antibodies are selected on the basis of their specificity for epitopes present on the neurotoxin but absent on the desired fragment, exemplified by $LH_N$ below. In the presence of partially purified $LH_N$, antibodies with specificity for the $H_C$ domain will only bind to the neurotoxin. Contaminating neurotoxin is removed from the $LH_N$ preparation by entrapment on the immobilised-antibody matrix, whereas $LH_N$, which is not recognised by the antibodies, does not interact with the column. This method is surprisingly efficient at removing residual toxicity from the $LH_N$ preparation and affords an effective purification technique. Entrapment of the neurotoxin contaminant by antibody binding, rather than specifically binding the $LH_N$, enables the elution conditions to be maintained at the optimum for $LH_N$ stability. The use of harsh elution conditions e.g. low pH, high salt, chaotropic ions, which may have detrimental effects on $LH_N$ polypeptide folding and enzymatic activity, are therefore avoided. Neurotoxin and other binding fragments may be eluted from the antibody column to release clostridial neurotoxin derivatives that are purified from derivatives deficient in the $H_C$ domain epitopes.

An additional advantage of the methods of the invention is thus that the desired component of the mixture that is being purified, that is to say the fragment or the conjugate or the other derivative, is that portion which is eluted from the column whereas the undesired portion, the toxin, remains bound to the column. This has the benefit that the desired material is less affected by the column and that no additional step, for example to elute bound, desired material from the column, is required as part of the method.

Further embodiments of the invention use two different affinity techniques in combination. In a preferred embodiment of the invention exemplified below, combinations of antibodies with different epitope recognition properties are used. By utilising monoclonal antibodies with different recognition epitopes, small conformational changes in neurotoxin can be accommodated. In this way, a greater proportion of neurotoxin is targeted for removal from the crude starting mixture.

It is further preferred that the method of the invention comprises an additional step, after separating the ligand from the toxin derivative preparation, which ligand we will refer to in these present paragraphs as the first ligand, of contacting the toxin derivative preparation with a second ligand, which selectively binds to the first ligand but not to the toxin derivative. It is occasionally the case that ligand attached, for example, to a chromatography column, detaches and thus the toxin derivative elutes from the column in combination with complexes of ligand and toxin. This opens the possibility of separation of the complex at a future time, releasing the toxin. It is an advantage of the preferred method of the invention that these ligand-toxin complexes, if present in the toxin derivative preparation are substantially removed by use of the further ligand.

The further, or second, ligand can suitably be an antibody that binds to the antibody used as the first ligand. A specific embodiment of the invention thus comprises:— preparing a toxin derivative preparation which comprises toxin derivative which is contaminated by low levels of toxin;

contacting the preparation with a ligand which selectively binds to the toxin but not to the toxin derivative;

separating the ligand from the toxin derivative preparation, thereby separating toxin from the toxin derivative preparation;

contacting the preparation with a further ligand that binds selectively to the first ligand, or binds selectively to a complex of the first ligand with toxin; and separating the second ligand from the toxin derivative preparation.

The first ligand can be an antibody which binds to an $H_C$ portion of the toxin, and the second ligand can be a further antibody or immunoglobulin binding domain which binds to the first antibody or to a complex of the first antibody with toxin, and in a specific example the second ligand can be protein G. In one particular example of the preferred embodiment of the invention in use, injection of 20 micrograms $LH_N$ purified according to the invention using the first ligand resulted in 0 out of 4 mice surviving, whereas use of the second ligand to remove antibody—toxin complexes resulted in 4 out of 4 survivors. This very surprising result exhibits the improved purity of the toxin derivative following application of the second purification step.

Specific antibodies or antibody fragments are optionally mixed with partially purified clostridial neurotoxin fragments in solution to form bound antibody-neurotoxin complexes. The antibody-neurotoxin complexes are then isolated from the mixture (e.g. by Protein G chromatography) and removed to yield purified agents in solution.

Immobilised monoclonal antibodies may be used specifically to bind contaminating neurotoxin and intact $H_C$ or other contaminants. Two BoNT/A $H_C$ specific monoclonal antibodies are thus utilised in a method that is surprisingly efficient at binding contaminating neurotoxin to prepare $LH_N/A$ of high purity and low toxicity.

The present invention is of application to any toxins which can be converted into useful fragments, conjugates and other derivatives, for example by proteolytic action, and is of particular application to clostridial neurotoxins, especially botulinum and tetanus toxins of all sub-groups.

By toxin derivative, it is intended to encompass all derivatives of a toxin that are prepared directly or indirectly from native toxin, for example by proteolytic action on the toxin, which methods can result in a preparation having residual, low levels of toxin present. Thus, a toxin derivative preparation according to the definition does not include recombinant toxin derivatives which are guaranteed to be free of toxin. The meaning of derivative thus encompasses toxin fragments and conjugates of toxin fragments with other molecules as well as variants of toxins and toxin fragments and conjugates.

In a further aspect, the invention provides an affinity chromatography column, for removal of toxin from a toxin derivative preparation, wherein the column comprises a ligand that selectively binds to toxin but not to the toxin derivative. This column is of use in separating toxin from toxin derivative, and the ligand employed is suitably an antibody or a metal ion.

A still further aspect of the invention lies in a toxin derivative preparation comprising 1–100 ppm toxin per toxin derivative, preferably 10–100 ppm. This preparation is derived from native toxin, and has a greatly reduced residual level of toxin.

A yet further aspect of the invention provides a composition comprising a derivative of a toxin and a pharmaceutically acceptable carrier, and further comprising a ligand that binds selectively to the toxin. The composition may for example comprise a conjugate of a toxin with a ligand that binds selectively to the toxin, wherein the toxin is bound non-covalently to the ligand. The toxin is thus neutralized by the ligand.

BRIEF DESCRIPTION OF THE SEVERAL VIEWS OF THE DRAWING

The invention is now described in specific embodiments, accompanied by drawings in which:—

EXAMPLE 1

Inhibition of Glycine Release

Embryonic spinal cord cells were treated for one day in the presence of 30 micrograms per ml of $LH_N/A$ (prior art preparation). This treatment resulted in an inhibition of glycine release of 64%. A parallel treatment was carried out in the presence of antibody 5BA 9.3, which binds specifically to botulinum neurotoxin A. This resulted in an inhibition of glycine release which was reduced to 44%.

EXAMPLE 2

Inhibition of Substance P Release

Embryonic Dorsal route ganglia were treated for 3 days with 20 micrograms per ml $LH_N/A$, $LH_N/A$+ antibody 5BA 9.3 and also with a conjugate of $LH_N/A$ with a targeting ligand in the presence of antibody 5BA 9.3.

The inhibition of substance P release was significant when the 20 µg/ml $LH_N/A$ fragment was used alone, and was at a level of about 26%. This level was reduced to about 4% in the presence of the specific antibody, and the level rose to about 21% when the conjugate (also 20 µg/ml) was used in the presence of the specific antibody.

EXAMPLE 3

Production of $LH_N/A$ from BoNT/A by Antibody-Affinity Chromatography

BoNT/A was prepared according to a previous method (Shone, C. C. and Tranter, H. S. (1995) in "Clostridial Neurotoxins—The molecular pathogenesis of tetanus and botulism", (Montecucco, C., Ed.), pp. 152–160, Springer). FPLC® chromatography media and columns were obtained from Amersham Pharmacia Biotech, UK. Affi-gel Hz™ matrix and materials were from BioRad, UK.

Preparation of an Anti-BoNT/A Antibody-Affinity Column

An antibody-affinity column was prepared with specific monoclonal antibodies essentially as suggested by the manufacturers' protocol. Briefly, monoclonal antibodies 5BA2.3 & 5BA9.3 which have different epitope recognition in the $H_c$ domain (Hallis, B., Fooks, S., Shone, C. and Hambleton, P. (1993) in "Botulinum and Tetanus Neurotoxins", (Das-Gupta, B. R., Ed.), pp. 433–436, Plenum Press, New York) were purified from mouse hybridoma tissue culture supernatant by Protein G (Amersham Pharmacia Biotech) chromatography. These antibodies represent a source of BoNT/A $H_C$-specific binding molecules and can be immobilised to a matrix or used free in solution to bind BoNT/A. In the presence of partially purified $LH_N/A$ (which has no $H_C$ domain) these antibodies will only bind to BoNT/A. The antibodies 5BA2.3 & 5BA9.3 were pooled in a 3:1 ratio and two mg of the pooled antibody was oxidised by the addition of sodium periodate (final concentration of 0.2%) prior coupling to 1 ml Affi-Gel Hz™ gel (16 hours at room temperature). Coupling efficiencies were routinely greater than 65%. The matrix was stored at 4° C. in the presence of 0.02% sodium azide.

Purification Strategy for the Preparation of Pure $LH_N/A$

BoNT/A was treated with 17 µg trypsin per mg BoNT/A for a period of 72–120 hours. After this time no material of 150 kDa was observed by SDS-PAGE and Coomassie blue staining. The trypsin digested sample was chromatographed (FPLC® system, Amersham Pharmacia Biotech) on a Mono Q® column (HR5/5) to remove trypsin and separate the majority of BoNT/A from $LH_N/A$. The crude sample was loaded onto the column at pH 7 in 20 mM HEPES, 50 mM NaCl and 2 ml $LH_N/A$ fractions eluted in a NaCl gradient from 50 mM to 150 mM. The slightly greater pI of BoNT/A (6.3) relative to $LH_N/A$ (5.2) encouraged any BoNT/A remaining after trypsinisation to elute from the anion exchange column at a lower salt concentration than $LH_N/A$. $LH_N/A$ containing fractions (as identified by SDS-PAGE) were pooled for application to the antibody column.

The semi-purified $LH_N/A$ mixture was applied and reapplied at least 3 times to a 1–2 ml immobilised monoclonal antibody matrix at 20° C. After a total of 3 hours in contact with the immobilised antibodies, the $LH_N/A$-enriched supernatant was removed. Entrapment of the BoNT/A contaminant, rather than specifically binding the $LH_N/A$, enables the elution conditions to be maintained at the optimum for $LH_N$ stability. The use of harsh elution conditions e.g. low pH, high salt, chaotropic ions, which may have detrimental effects on $LH_N$ polypeptide folding and enzymatic activity, are therefore avoided. Treatment of the immobilised antibody column with 0.2M glycine/HCl pH2.5 resulted in regeneration of the column and elution of BoNT/A-reactive proteins of 150 kDa.

The $LH_N/A$ enriched sample was then applied 2 times to a 1 ml HiTrap® Protein G column (Amersham Pharmacia Biotech) at 20° C. Protein G was selected since it has a high affinity for mouse monoclonal antibodies. This step was included to remove BoNT/A-antibody complexes that may leach from the immunocolumn. Antibody species bind to the Protein G matrix allowing purified $LH_N/A$ to elute.

Figure 1:
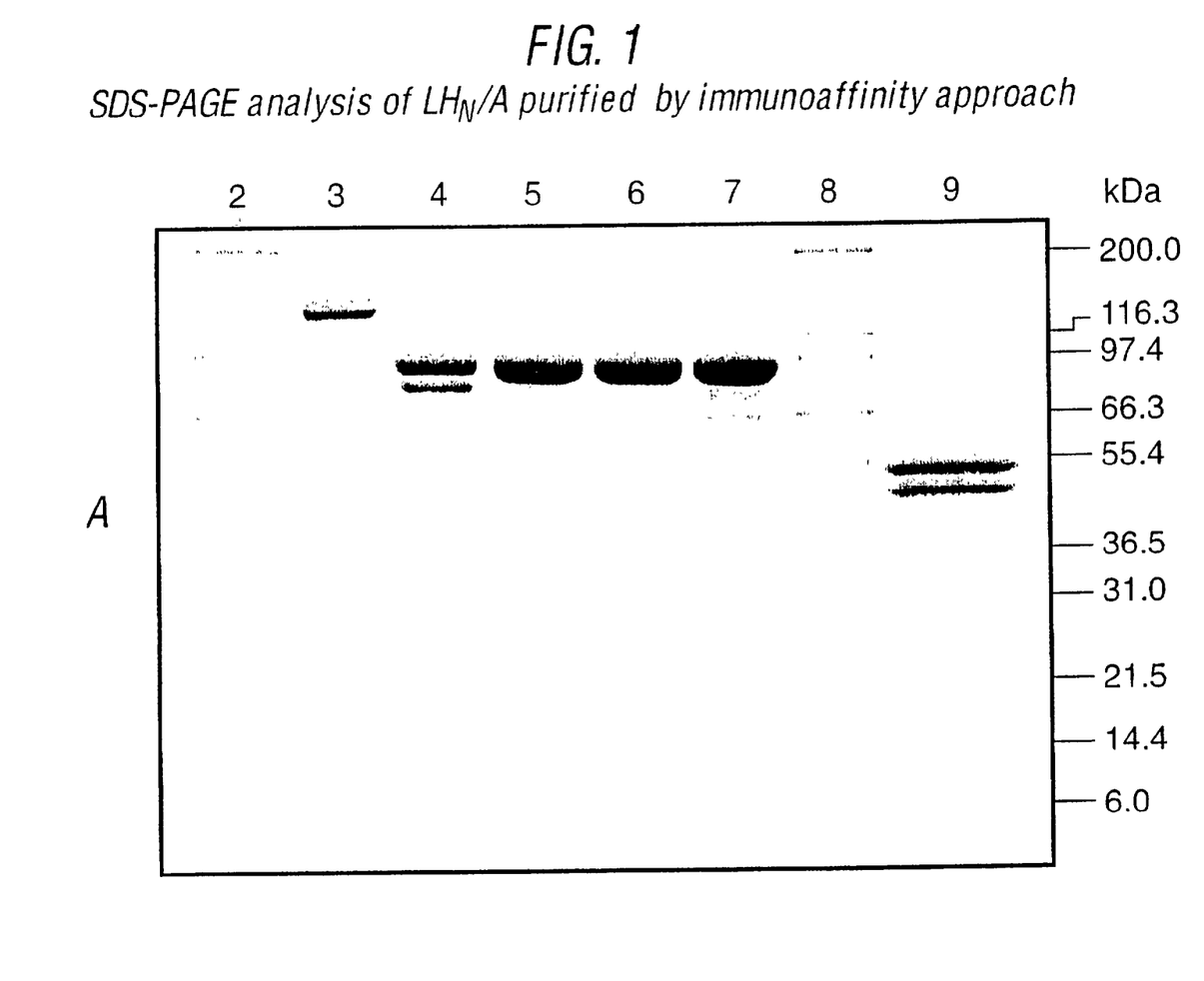
FIGS. 1A and 1B show SDS-PAGE analysis of $LH_N/A$ purified by the immunoaffinity approach.

The profile of the purification procedure is illustrated by the SDS-PAGE analysis in FIG. 1. Trypsin digested BoNT/A (lane 4) was applied to a Mono Q® anion exchange column and fractions harvested (lane 5). Material pre- and post-Protein G is indicated in lanes 6 and 7 respectively. Lane 7 represents the final purified $LH_N/A$ preparation. Samples were analysed by SDS-PAGE on 4–20% polyacrylamide and stained with Coomassie blue (Panel A), or Western blotted and probed with anti-BoNT/A (Panel B). Molecular weight markers are indicated on the Figure with reference to the standards in lanes 2 & 8. Molecular weight markers in lane 1 are compatible with enhanced chemiluminescence and are for visualisation purposes only.

In Vitro SNAP-25 Peptide Cleavage

Figure 2:
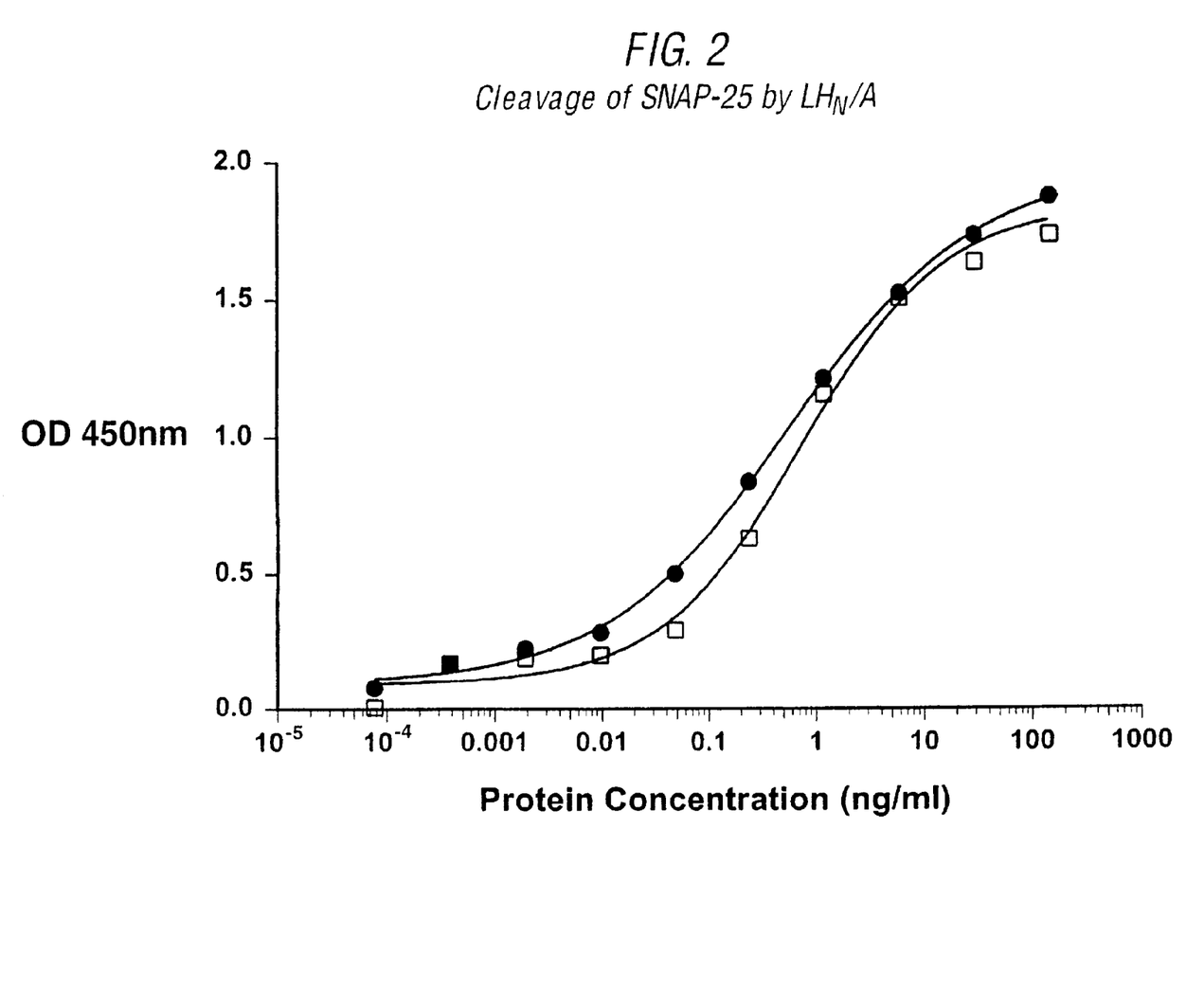
FIG. 2 shows retention of functional activity of $LH_N/A$ prepared by the invention

The in vitro cleavage of SNAP-25 by $LH_N/A$ and other endopeptidase samples were assessed essentially as described previously (Hallis, B., James, B. A. F. and Shone, C. C. (1996) *J. Clin. Microbiol.* 34, 1934–1938). FIG. 2 clearly demonstrates the similarity in catalytic activity between purified LH$_N$/A and reduced BoNT/A. A series of LH$_N$/A (●) and BoNT/A (□) dilutions were incubated for 1 hour prior to assessment of SNAP-25 cleavage. The data is representative of at least 7 experiments which have suggested EC$_{50}$ for LH$_N$/A and BoNT/A to be 3.8±0.7 pM and 3.6±0.6 pM respectively.

SDS-PAGE and Western Blotting

SDS-PAGE and Western Blotting were performed using standard protocols.

Proteins were resolved on a 4–20% Tris/glycine polyacrylamide gel (Novex) and either stained by the addition of Coomassie blue or transferred to nitrocellulose. Positive binding of antibodies was detected by enhanced chemiluminescence.

EXAMPLE 4

Production of LHN/A from BoNT/A by Immobilised Metal Affinity Chromatography

BoNT/A was prepared according to a previous method (Shone, C. C. and Tranter, H. S. (1995) in "Clostridial Neurotoxins—The molecular pathogenesis of tetanus and botulism", (Montecucco, C., Ed.), pp. 152–160, Springer). FPLC® chromatography media and columns were obtained from Amersham Pharmacia Biotech, UK. Affi-gel Hz™ matrix and materials were from BioRad, UK.

Preparation of Cationic Metal Affinity Column

An affinity column was prepared essentially as suggested by the manufacturers' protocol. Briefly, chelating Sepharose® (Amersham Pharmacia Biotech) was washed with 50 mM EDTA+1M NaCl (10 column volumes), washed with 10 column volumes ultra-high purity water, primed with 5 mg/ml ZnCl$_2$ (10 column volumes–neutral pH, filtered), and finally washed with purified water (10× column volumes).

Purification Strategy for the Preparation of Pure LH$_N$/A

BoNT/A was treated with 17 μg trypsin per mg BoNT/A for a period of 72–120 hours. After this time no material of 150 kDa was observed by SDS-PAGE and Coomassie blue staining. The trypsin digested sample was chromatographed (FPLC® system, Amersham Pharmacia Biotech) on a Mono Q® column (HR5/5) to remove trypsin and separate the majority of BoNT/A from LH$_N$/A. The crude sample was loaded onto the column at pH 7 in 20 mM HEPES, 50 mM NaCl and 2 ml LH$_N$/A fractions eluted in a NaCl gradient from 50 mM to 150 mM. The slightly greater pI of BoNT/A (6.3) relative to LH$_N$/A (5.2) encouraged any BoNT/A remaining after trypsinisation to elute from the anion exchange column at a lower salt concentration than LH$_N$/A. LH$_N$/A containing fractions (as identified by SDS-PAGE) were pooled for application to the metal affinity column.

For the purification of 1 mg LH$_N$/A a 1 ml column of Zn$^{2+}$ primed chelating Sepharose®, prepared as described above was equilibrated to the appropriate pH (7.5–8.5) using 50 mM HEPES+1M NaCl ('equilibration buffer'). 1 mg of LH$_N$ (post Mono Q® fractionation) was applied to the column after dialysis against the appropriate equilibration buffer. Material that did not bind was recovered and the column washed with excess equilibration buffer. Bound material was eluted by the application of equilibration buffer supplemented with 10 mM EDTA.

Another suitable method is described by Rossetto et al, Biochem J., (1992), vol. 285, pp 9–12.

EXAMPLE 5

Evaluation of BoNT/A Contamination Levels in LH$_N$/A Prepared by Immunocolumn Chromatography in Primary Cultures of Spinal Cord Neurons Inhibition of [$^3$H]-Glycine Release from eSCN Spinal cord neurons are exquisitely sensitive to neurotoxin, with an IC$_{50}$ of inhibition of glycine release of 0.027±0.0006 pM after 3 days exposure to BoNT/A (unpublished observations). Therefore they serve as a suitably sensitive assay for screening samples for the presence of neurotoxin. Spinal cords dissected from 14–15 day old foetal Sprague Dawley rats were cultured for 21 days using a modification of previously described method (Ransom, B. R., Neale, E., Henkart, M., Bullock, P. N. and Nelson, P. G. (1977) J. Neurophysiol. 40, 1132–1150 & Fitzgerald, S. C. (1989) "A dissection and tissue culture manual of the nervous system", Alan R. Liss, Inc., New York, N.Y.). Cells were loaded with [$^3$H]-glycine for 30 minutes prior to determination of basal and potassium-stimulated release of transmitter (essentially as described in Williamson, L. C., Halpern, J. L., Montecucco, C., Brown, J. E. and Neale, E. A. (1996) J. Biol. Chem. 271, 7694–7699). A sample of 0.2M NaOH-lysed cells was used to determine total counts, from which % release could be calculated.

Figure 3:
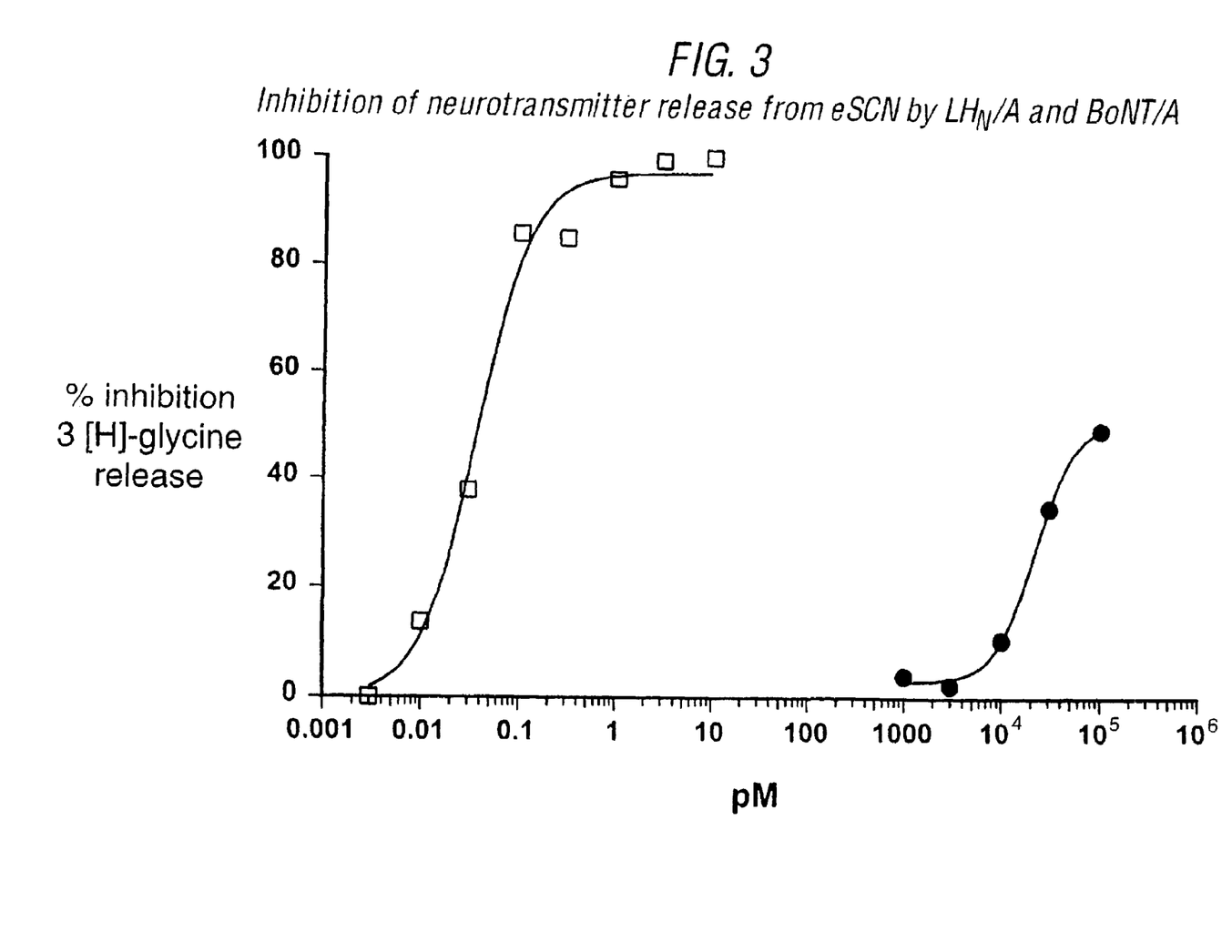
FIG. 3 shows inhibition of neurotransmitter release from eSCN by $LH_N/A$ and BoNT/A.

In FIG. 3 there is shown a comparison of the inhibition curves obtained after 3 days incubation of spinal cord neurons with LH$_N$/A and BoNT/A. Samples of LH$_N$/A (●) or BoNT/A (□) were diluted in eSCN growth medium and 1 ml of the appropriate concentration applied. Cells were incubated for three days prior to assessment of [$^3$H]-glycine release. The % inhibition data is calculated by relating the net stimulated [$^3$H]-glycine release to the total uptake and then expressing this as a percentage of the release obtained from control media treated cells. The data are representative of at least three experiments. The IC$_{50}$ data determined for LH$_N$/A (106.2±49.3 nM) and BoNT/A can be used to estimate the ratio of BoNT/A to LH$_N$/A in the purified material. It is estimated that a maximum of 1 BoNT/A molecule per 4×10$^6$ LH$_N$/A molecules was present in the final purified material.

EXAMPLE 6

Removal of BoNT/A from LH$_N$/A Preparations as Assessed by Mouse Lethality

Residual BoNT/A contamination was evaluated following intraperitoneal injection of 0.5 ml of test sample in gelatine-phosphate buffer (1% (w/v) Na$_2$HPO$_4$, 0.2% (w/v) gelatine, pH 6.5–6.6) into mice. After 4 days the number of surviving animals was counted. Literature precedents (Shone et al. 1987 & de Pavia, A. and Dolly, J. O. 1990) cite the LD$_{50}$ to be the concentration of test sample that killed half the animals in the test group within 4 days. By this analysis, batches of purified LH$_N$/A were demonstrated to exhibit an LD$_{50}$ of approximately 50 μg/mouse i.e. approximately 20 LD$_{50}$/mg. This is significantly lower than previously reported LD$_{50}$ data for LH$_N$/A (6000–12000 LD$_{50}$/mg by Shone, C. C., Hambleton, P. and Melling, J. (1987) Eur. J. Biochem. 167, 175–180) and LC/A (<100 LD$_{50}$/mg in Shone et al. 1987 & 10000 LD$_{50}$/mg in de Pavia, A. and Dolly, J. O. (1990) FEBS Lett., 277, 171–174).

Figure 4:
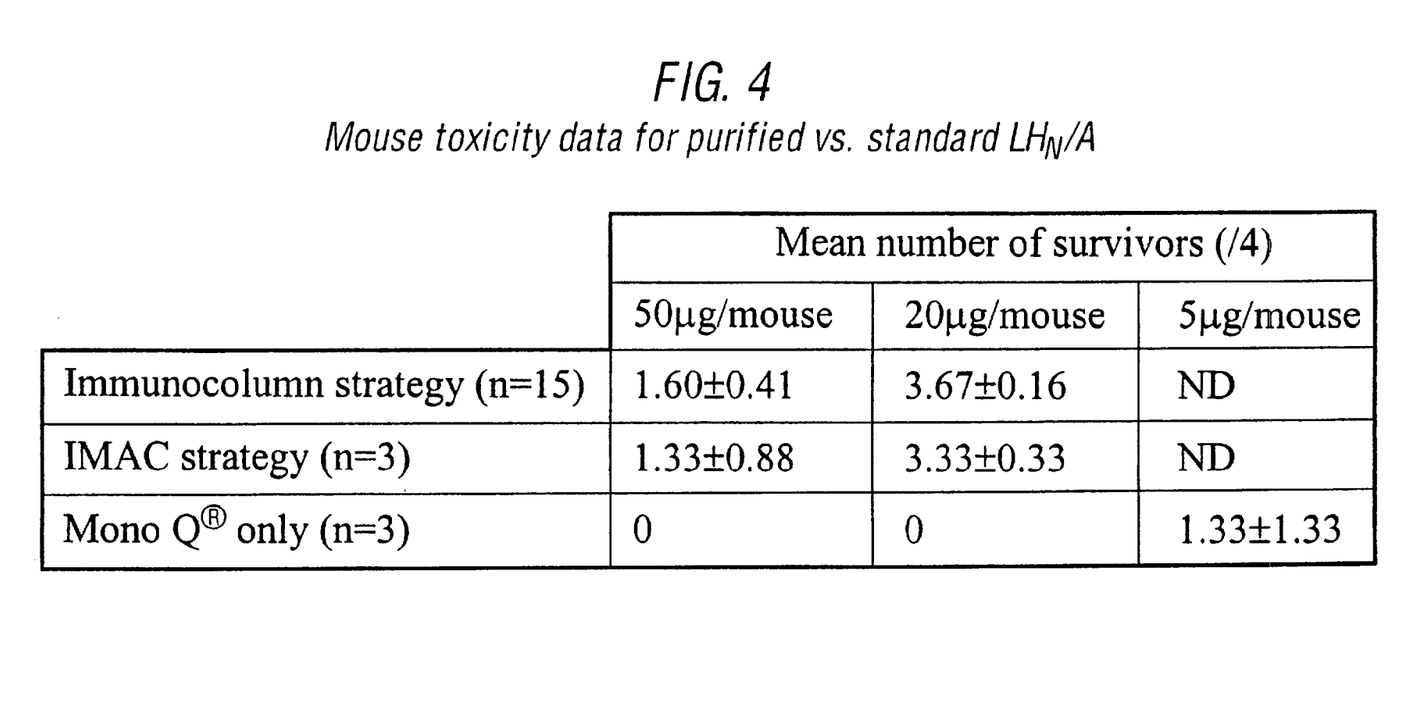
FIG. 4 shows mouse toxicity data for purified $LH_N/A$.

As an alternative method of data analysis, the mean number of survivors from different batches of $LH_N/A$ was determined and is presented in FIG. 4 (Abbreviations: IMAC; immobilised metal affinity column, ND; Not determined). These data clearly demonstrate the significantly low toxicity of the $LH_N/A$ prepared by both exemplified methods of purification.

The invention claimed is:

1. A method of removing residual clostridial neurotoxin from a preparation of $LH_N$ of clostridial neurotoxin comprising:
   (i) applying a preparation comprising $LH_N$ of clostridial neurotoxin to a first affinity column, wherein said first affinity column comprises a first ligand immobilized on said first affinity column, and wherein said first ligand selectively binds to the residual clostridial neurotoxin but does not bind to the $LH_N$, thereby forming an immobilized first ligand-clostridial neurotoxin complex, and an eluate comprising the $LH_N$, wherein said eluate may contain an amount of the first ligand-clostridial neurotoxin complex that has become detached from the first affinity column;
   (ii) contacting said eluate with a second affinity column, wherein said second affinity column comprises a second ligand immobilized on said second affinity column, and wherein said second ligand selectively binds to the first ligand-clostridial neurotoxin complex, if present in the eluate, but does not bind to the $LH_N$ present in the eluate; and
thereby removing the residual clostridial neurotoxin from the preparation of the $LH_N$.

2. The method of claim 1, wherein the first ligand is an antibody.

3. The method of claim 1, wherein the first ligand is a metal ion.

4. The method of claim 1, wherein the second ligand is an antibody.

5. The method of claim 1, wherein the second ligand is Protein G.

6. A method of removing residual clostridial neurotoxin from a preparation of $LH_N$ of clostridial neurotoxin comprising:
   (i) applying a preparation comprising $LH_N$ of clostridial neurotoxin to a first affinity column, wherein said first affinity column comprises a first ligand immobilized on said first affinity column, and wherein said first ligand selectively binds to the residual clostridial neurotoxin but does not bind to the $LH_N$, thereby forming an immobilized first ligand-clostridial neurotoxin complex, and an eluate comprising the $LH_N$, wherein said eluate may contain an amount of the first ligand-clostridial neurotoxin complex that has become detached from the first affinity column;
   (ii) contacting said eluate with a second affinity column, wherein said second affinity column comprises a second ligand immobilized on said second affinity column, and wherein said second ligand selectively binds to the first ligand of the first ligand-clostridial neurotoxin complex, if present in the eluate, but does not bind to the $LH_N$ present in the eluate; and
thereby removing the residual clostridial neurotoxin from the preparation of the $LH_N$.

7. The method of claim 6, wherein the first ligand is an antibody.

8. The method of claim 6, wherein the first ligand is a metal ion.

9. The method of claim 6, wherein the second ligand is an antibody.

10. The method of claim 6, wherein the second ligand is Protein G.

* * * * *